United States Patent
Lee et al.

(10) Patent No.: US 11,740,113 B2
(45) Date of Patent: Aug. 29, 2023

(54) MICRONEEDLE PROBE FOR MEASURING SAP FLOW OF PLANT, AND SAP FLOW MEASURING DEVICE HAVING SAME

(71) Applicant: TELOFARM, Inc., Seoul (KR)

(72) Inventors: Jung Hoon Lee, Seoul (KR); Jung Ho Lee, Gyeonggi-do (KR)

(73) Assignee: TELOFARM, Inc., Seoul (KR)

( * ) Notice: Subject to any disclaimer, the term of this patent is extended or adjusted under 35 U.S.C. 154(b) by 0 days.

(21) Appl. No.: 17/239,610

(22) Filed: Apr. 25, 2021

(65) Prior Publication Data

US 2022/0187113 A1     Jun. 16, 2022

Related U.S. Application Data

(63) Continuation of application No. 16/069,430, filed as application No. PCT/KR2017/000365 on Jan. 11, 2017, now Pat. No. 11,015,965.

(30) Foreign Application Priority Data

Jan. 12, 2016    (KR) ........................ 10-2016-0003836
Jan. 29, 2016    (KR) ........................ 10-2016-0012004

(51) Int. Cl.
    *G01F 1/684*        (2006.01)
    *A01G 7/00*         (2006.01)
    *A01G 23/10*        (2006.01)
    *G01F 1/688*        (2006.01)
    *G01F 1/69*          (2006.01)
              (Continued)

(52) U.S. Cl.
    CPC ............... *G01F 1/684* (2013.01); *A01G 7/00* (2013.01); *A01G 23/10* (2013.01); *G01F 1/688* (2013.01); *G01F 1/6845* (2013.01); *G01F 1/69* (2013.01); *G01F 1/692* (2013.01); *G01K 7/16* (2013.01); *G01K 13/02* (2013.01); *G01N 27/07* (2013.01);
(Continued)

(58) Field of Classification Search
    CPC ........ G01F 1/684; G01F 1/6845; G01F 1/688; G01F 1/69; G01F 1/692; G01F 15/006; G01N 27/07; G01N 27/08; G01N 27/14; G01N 33/00; G01K 7/16; G01K 13/02; A01G 23/10
See application file for complete search history.

(56) References Cited

U.S. PATENT DOCUMENTS 5,452,610 A    9/1995    Kleinhans et al.
2013/0098150 A1    4/2013    Sella
(Continued)

FOREIGN PATENT DOCUMENTS

EP         1187653 B1     3/2010
JP        2008233047 A    10/2008
(Continued)

OTHER PUBLICATIONS

First Office Action of China National Intellectual Property Administration Application No. 2017800130609 dated Apr. 13, 2020.
(Continued)

*Primary Examiner* — Benjamin R Schmitt
(74) *Attorney, Agent, or Firm* — Welsh IP Law LLC

(57) ABSTRACT

A microneedle probe for measuring a sap flow in a plant is disclosed, the microneedle probe including: a substrate; and a sensor unit which is installed on the substrate, generates heat, and measures a temperature that changes in accordance with a sap flow.

17 Claims, 4 Drawing Sheets

(51) Int. Cl.
*G01F 1/692* (2006.01)
*G01K 13/02* (2021.01)
*G01K 7/16* (2006.01)
*G01N 33/00* (2006.01)
*G01N 27/07* (2006.01)
*G01N 27/08* (2006.01)
*G01N 27/14* (2006.01)
*G01F 15/00* (2006.01)

(52) U.S. Cl.
CPC ............ *G01N 27/08* (2013.01); *G01N 27/14* (2013.01); *G01N 33/00* (2013.01); *G01F 15/006* (2013.01)

(56) References Cited

U.S. PATENT DOCUMENTS

| | | |
|---|---|---|
| 2016/0095541 A1 | 4/2016 | Wang et al. |
| 2017/0010296 A1 | 1/2017 | Shimokawa et al. |
| 2017/0030751 A1 | 2/2017 | Liu et al. |

FOREIGN PATENT DOCUMENTS

| | | |
|---|---|---|
| JP | 2014211407 A | 11/2014 |
| JP | 2015145810 A | 8/2015 |
| KR | 20100059577 A | 6/2010 |
| KR | 20140078644 A | 6/2014 |

OTHER PUBLICATIONS

Korean Office Action Application No. 10-2016-0012003 dated Oct. 28, 2016 12 pages (first six pages are machine translation by Google, second six pages are KR OA).

MICRONEEDLE PROBE FOR MEASURING SAP FLOW OF PLANT, AND SAP FLOW MEASURING DEVICE HAVING SAME

TECHNICAL FIELD

The present invention relates to a device for measuring biological information of a plant, particularly, a microneedle probe for measuring a flow of sap flowing in a xylem of a plant, and a sap flow measuring device having the same.

BACKGROUND

A plant growth model directly affects production and quality of plants. Examples of biological information of the plant, which mainly affect the plant growth, include a temperature, a sap flow (SF), and electrical conductivity (EC), and based on the biological information of the plant, a water supply schedule, control of temperature and light amount, a timing of supplying a fertilizer, the amount of fertilizer to be supplied, and the like are determined, thereby determining the plant growth model.

The measurement for the plant growth model has been limited to external environmental variables such as temperatures and humidity, destructive measurement, indirect measurement, or the like, and traditionally, methods of measuring the electrical conductivity by using moisture in soil, metered water consumption, and plant samples made as sap have been used. However, these methods have provided insufficient conditions in acquiring indirect or detailed information and predicting reactions in the plants.

As a technology for measuring a biological signal in a plant, a technology, which measures the biological signal by inserting a probe directly into a stem of a plant, has been developed, such that a sap flow in the plant is directly measured and used, but in all cases, this direct measurement uses a device in the form of an invasive needle.

As the methods of measuring a sap flow, there have been used (i) a heat pulse (HP) technology which applies a periodic heat pulse to a plant by using an invasive probe, and calculates flow density by detecting a movement of the heat pulse in accordance with a sap flow in the plant by using a temperature probe, (ii) a heat dissipation (HD) technology which continuously applies heat to a plant by using an invasive probe, and measures and calculates, from a temperature difference, a degree to which the heat is dissipated at night in the case of absence of the sap flow and the case of presence of the sap flow, (iii) a heat field deformation (HFD) technology which configures an invasive probe having a temperature measuring probe and a heater probe, and calculates sap flow density by measuring, by using the temperature measuring probe, a degree to which a heat field, which is created by heat generated by a heater at a center, is deformed due to a sap flow, and (iv) a stem heat balance (SHB) technology which uses a temperature difference between upper and lower portions of a stem which is caused by a sap flow and heat generated by a heater installed outside the stem of the plant.

However, because most of the technologies use the needle and the needle is configured in a very invasive form to the extent that the needle has a diameter of 1 to 5 mm, these technologies are limitedly used only for types of trees, and it is difficult to measure biological information by inserting the invasive probe having a diameter of 1 to 5 mm into plants such as fruit vegetables such as tomato plants and paprika plants, and flowers. In addition, because a measurement device is large in size, expensive, and complicated, there is a problem in that it is difficult to apply the measurement device to various sites of one crop or to various crops at one time, and as a result, there is a problem in that reliability of measurement results acquired by using a small number of specimens is insufficient, and there is also a problem in ensuring statistical meaningfulness.

However, an innovation in agriculture has been rapidly promoted in virtue of developments of various types of scientific technologies starting with biology after the Industrial Revolution. In particular, the technology related to the plant growth also marks a new era along with developments of agriculture, ICT-based MEMS, and nanotechnologies.

There is a need for a development of a technology capable of measuring biological information of various plants including trees by using a minimally invasive technology, and to this end, it is necessary to implement a precise measurement technology using a combination of the micro electro mechanical systems (MEMS) and the nanotechnologies.

More specifically, to meet the minimally invasive requirements, a size of a sensor to be inserted into a plant needs to be decreased to a microscale level, such a microneedle probe needs to be manufactured by using the MEMS technology which is a silicon process technology, and a shape, a size, and the like of the microneedle probe need to be suitable for a relationship with tissue of the plant.

Furthermore, unlike the related art, functional sensor elements capable of measuring a temperature, a sap flow (SF), electrical conductivity (EC), and the like need to be integrated into the microneedle probe, and nanostructures, membranes, and the like need to be designed and integrally manufactured in order to implement the functions within a reliable and desired range.

SUMMARY

An object of the present invention is to provide a technology capable of directly measuring, from a plant, biological information essential to a growth model of the plant in a minimally invasive manner so that the technology may be applied to plants such as fruit vegetables such as tomato plants and paprika plants and flowers as well as trees.

In addition, another object of the present invention is to provide a technology capable of ensuring measurement reliability by making a measurement device have a microscale and compact size such that the measurement device is easily applied to various sites of one crop or to various crops simultaneously.

To this end, the present invention provides a microneedle probe for measuring a sap flow in a plant, the microneedle probe including: a substrate; and a sensor unit which is installed on the substrate, generates heat, and measures a temperature that changes in accordance with a sap flow.

In addition, the present invention provides the microneedle probe further including a protective wall which is installed to protrude on the substrate and protects the sensor unit when the microneedle probe is inserted into and remains in the plant.

In addition, the present invention provides the microneedle probe in which one end portion of the substrate is sharpened.

In addition, the present invention provides the microneedle probe in which a thin portion, which is positioned at a side of the substrate which is inserted into the plant, has a smaller thickness than a thick portion positioned opposite to the thin portion.

In addition, the present invention provides the microneedle probe in which a protruding portion is formed in a longitudinal direction of the substrate on a base portion which is positioned at a side opposite to a side of the substrate, which is inserted into the plant, and has an inclined surface tapered such that a size in a width direction of the substrate is gradually increased.

In addition, the present invention provides the microneedle probe in which the sensor unit includes two temperature measuring sensors which face each other, and a heater which is positioned between the two temperature measuring sensors.

In addition, the present invention provides the microneedle probe in which the temperature measuring sensor of the sensor unit uses a temperature coefficient of resistance of a metal pattern.

In addition, the present invention provides the microneedle probe in which the multiple sensor units are installed in a longitudinal direction of the substrate.

In addition, the present invention provides the microneedle probe in which the protective walls are installed at front and rear sides of the sensor unit in a longitudinal direction of the substrate.

In addition, the present invention provides the microneedle probe further including: a cavity which is formed in the substrate; and a suspension which is installed on the cavity, in which the sensor unit is installed on the suspension such that heat transfer between the sensor unit and the substrate is prevented.

In addition, the present invention provides the microneedle probe in which the suspension is formed as a thin film made of anodized aluminum oxide and silicon nitride (SiN).

In addition, the present invention provides the microneedle probe further including a contact pad which connects a BUS line, which is connected to the sensor unit, to an external terminal and packages the BUS line.

In addition, the present invention provides a device for measuring a sap flow in a plant, the device including: a current generating unit which generates a current; a power supply unit which supplies power required to operate the current generating unit; a microneedle probe which receives the current from the current generating unit and constitutes a measurement circuit by being inserted into a plant and coming into contact with sap in a xylem; and a control unit which calculates sap flow density based on a value measured by a sensor unit of the microneedle probe.

In addition, the present invention provides the device for measuring a sap flow in a plant, in which the multiple microneedle probes are provided to calculate the sap flow at multiple points in the plant.

In addition, the present invention provides a method of manufacturing a microneedle probe for measuring a sap flow in a plant, the method including: forming a silicon oxidation layer on a substrate; forming a suspension, which is formed as a porous thin film, on the silicon oxidation layer; and forming a sensor unit on the suspension by patterning the sensor unit.

In addition, the present invention provides the method of manufacturing a microneedle probe, the method further including: forming a protective wall, which protects the sensor unit, at a front side and/or a rear side of the sensor unit in a longitudinal direction of the substrate.

In addition, the present invention provides the method of manufacturing a microneedle probe, the method further including: forming a cavity by etching the substrate which is positioned below the suspension.

In addition, the present invention provides the method of manufacturing a microneedle probe, the method further including: sharpening one end portion of the substrate by performing silicon impurity doping and selective etching.

According to the present invention, it is possible to reliably measure biological information of a plant, particularly, a sap flow by using the microneedle probe that may be applied to the plant in a minimally invasive manner.

In addition, according to the present invention, it is possible to reduce a size of the measurement device and make the measurement device have a compact size since the sensor elements, which may measure the sap flow, are integrally configured on the microneedle probe.

In addition, according to the present invention, the types of plants, of which the sap flow may be directly measured, may be extended and applied to not only trees, but also crops, such as fruit vegetables such as tomato plants and paprika plants or flowers, which have stems with small diameters and are not hard.

In addition, according to the present invention, the sap flows at various sites of one crop may be measured, and the sap flows in various crops may be measured, and as a result, it is possible to further improve reliability of the measured values.

DETAILED DESCRIPTION

Figure 1:
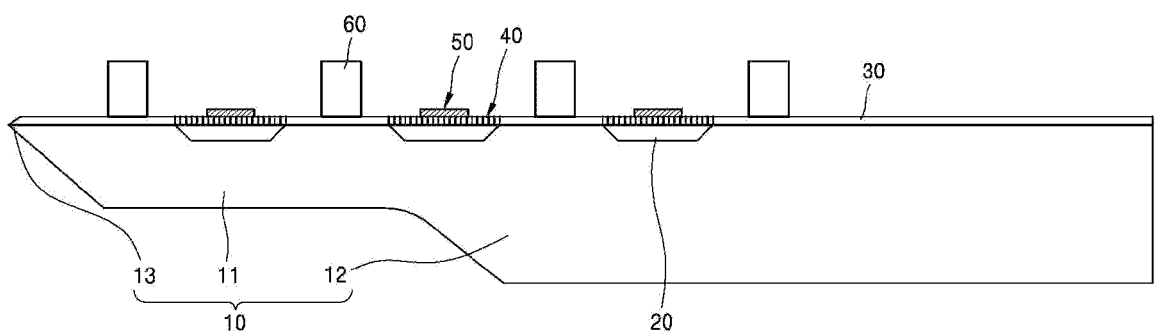
FIG. 1 illustrates a longitudinal cross-sectional view of an exemplary embodiment of a microneedle probe according to the present invention.

The present invention will be apparent with reference to exemplary embodiments to be described below in detail together with the accompanying drawings.

However, the present invention is not limited to exemplary embodiments disclosed herein, but will be implemented in various forms, the exemplary embodiments are provided so as to completely disclose the present invention and to completely inform a person with ordinary skill in the art to which the present invention pertains with the scope of the present invention, and the present invention will be defined only by the scope of the appended claims.

Meanwhile, the terms used in the present specification are for explaining the exemplary embodiments, not for limiting the present invention. From this point of view, a singular form also includes a plural form in the present specification unless particularly stated otherwise. In addition, the terms such as "comprises (includes)" and/or "comprising (including)" used in the specification do not exclude presence or addition of one or more other constituent elements, steps, operations, and/or elements, in addition to the mentioned constituent elements, steps, operations, and/or elements. The terms such as "first" or "second" may be used to describe various constituent elements, but the meanings of the constituent elements should not be limited by the terms. The terms are used only for the purpose of discriminating one constituent element from another constituent element.

An exemplary embodiment of the present invention is to measure biophysical and biochemical information which is applicable even to plants such as fruit vegetables such as tomato plants and paprika plants or flowers.

In particular, in the exemplary embodiment of the present invention, a microscale needle probe is inserted into a stem of a plant and approaches a xylem of the plant, thereby measuring a flow of sap flowing in the xylem.

The microscale needle probe is required to measure biological information such as a sap flow in a fruit vegetable plant such as a tomato plant having a stem thinner than a stem of a tree.

The microscale needle probe may be inserted and maintained into the stem of the plant having fine tissue. A needle having a large diameter (diameter of 1 to 5 mm), which is used for a sap flow measuring device in the related art that measures a tree which is hard and large in size, is not suitable for the plant having fine tissue.

According to the exemplary embodiment of the present invention, the needle probe needs to have a microscale and small size to perform the measurement under a minimally invasive condition. A range of a dimension of the needle probe may be 1 to 6 mm in a longitudinal direction, 100 to 200 μm in a thickness direction, and 200 to 400 μm in a width direction.

Hereinafter, a configuration of the microneedle probe according to the exemplary embodiment of the present invention and a configuration of a sap flow measuring device having the microneedle probe will be described more specifically.

Figure 2:
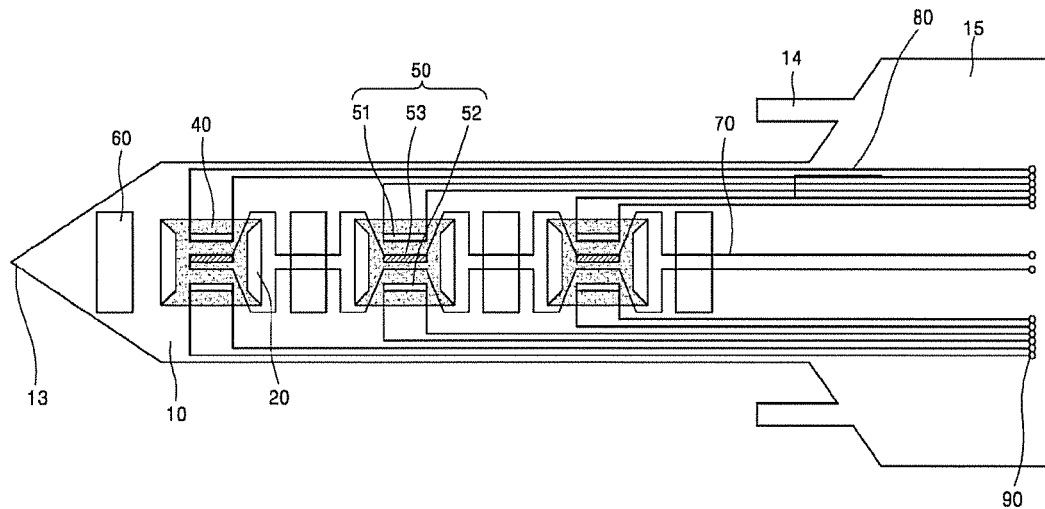
FIG. 2 illustrates a top plan view of the exemplary embodiment of the microneedle probe according to the present invention.

FIGS. 1 and 2 are a cross-sectional view and a top plan view illustrating a detailed configuration of the microneedle probe according to the exemplary embodiment of the present invention.

A microneedle probe 1 according to the exemplary embodiment of the present invention may be manufactured by using a silicon-based MEMS process.

The microneedle probe 1 is configured to be inserted into a xylem (vessel) of a plant to be measured and to measure a flow of sap flowing in the xylem in a minimally invasive manner. The microneedle probe 1 has a substrate 10. The substrate 10 may be made of silicon. An end portion 13 of one end of the substrate 10, which is inserted into a plant body, is sharpened to a level of an atom, such that the microneedle probe 1 may be easily inserted into the plant body. To sharpen the end portion of the substrate 10, a degree to which the end portion 13 is sharp may be adjusted by silicon impurity doping and selective etching during a manufacturing process.

In addition, a thin portion 11 at a side of the substrate 10, which is inserted into the plant body, may be formed to have a smaller thickness than a thick portion 12 opposite to the thin portion 11. With the configuration as described above, the thin portion 11 of the microneedle probe 1 may easily penetrate into and be inserted into the tissue of the plant. The thick portion 12 remains thicker than the thin portion 11, thereby maintaining rigidity of the substrate 10. According to the exemplary embodiment, the substrate 10 may be manufactured such that the thin portion 11 of the substrate 10 has a thickness of 100 μm as a numerical value and the thick portion 12 of the substrate 10 has a thickness of 200 μm as a numerical value.

A base portion 15 of the substrate 10, which is positioned opposite to the end portion of the substrate 10 which is inserted into the plant body, has an inclined surface tapered such that a size of the microneedle probe 1 is gradually increased in a width direction, and as a result, it is possible to ensure rigidity so that the microneedle probe 1 is not broken at the time of inserting the microneedle probe 1 into the plant body or measuring the sap flow. In addition, protruding portions 14 may protrude from the inclined surface of the base portion 15 in a longitudinal direction of the microneedle probe 1, and the protruding portions 14 may have symmetric shapes and sizes based on a centerline in the longitudinal direction of the microneedle probe 1. Because the protruding portions 14 are also inserted into the plant body when the microneedle probe 1 is inserted into the plant body, the microneedle probe 1 is securely fixed to the plant body, such that the microneedle probe 1 may perform accurate measurement over a long period of time without being broken.

Sensor units 50 capable of measuring the sap flow may be installed on the substrate 10.

The sensor unit 50 may include two temperature measuring sensors 51 and 52, and a heater 53 positioned between the temperature measuring sensors 51 and 52. The temperature measuring sensors 51 and 52 and the heater 53 may be formed as micro metal patterns and may have a triplet shape in which lines are formed adjacent to one another. The sensor unit 50 may be installed on the substrate 10 so that a longitudinal direction of the substrate 10 is in parallel with a longitudinal direction of the triplet shape. In the case in which the sensor unit 50 is configured as described above, when inserting the microneedle probe 1 into the plant body, an upper surface of the substrate 10 of the microneedle probe 1 is in parallel with a longitudinal direction of a stem of the plant body, such that the sap may flow via the sensor unit 50 in the order of the temperature measuring sensor 51 or 52, the heater 53, and the temperature measuring sensor 52 or 51 of the sensor unit 50 when the sap flows in the xylem in the longitudinal direction of the stem.

The temperature measuring sensors 51 and 52 according to the exemplary embodiment of the present invention may be configured to measure a change in resistance caused by a change in temperature by using a temperature coefficient of resistance of the pattern of metal such as platinum. In addition, a thermocouple may be used as the temperature measuring sensors 51 and 52.

In the exemplary embodiment of the present invention, the sensor unit 50 includes the two temperature measuring sensors 51 and 52 and the heater 53 positioned between the temperature measuring sensors 51 and 52, but instead of the two temperature measuring sensors 51 and 52 and the heater 53, a principle may be used in which a single resistance line, which is made of platinum, like a hot wire anemometer, is heated and placed in a direction perpendicular to the flow of the sap, such that the resistance line loses heat so that a temperature is changed and resistance is also changed. In this case, the single resistance line may be substituted for the sensor unit 50.

As illustrated in FIG. 1, according to the exemplary embodiment of the present invention, the multiple sensor units 50 may be installed in the longitudinal direction of the substrate 10 and configured to measure the sap flow at multiple points.

When the microneedle probe 1 is inserted into the plant body and remains for monitoring, protective walls 60 for protecting the sensor unit 50 may be installed. The protective wall 60 may be formed as a polymer pattern on the substrate 10. In the exemplary embodiment, a height of the protective wall 60 may be 50 μm as a numerical value, and a dimension of the protective wall 60 is set to be equal to or larger than a dimension, that is, a height and a width of the sensor unit 50, thereby further improving the protection effect. The protective wall 60 may be installed at a front side and/or a rear side of the sensor unit 50 in the longitudinal direction of the substrate 10.

The protective wall 60 may serve to not only protect the sensor unit 50, but also scrape the tissue of the plant when the microneedle probe 1 is inserted into the plant body, thereby enabling the microneedle probe 1 to be easily inserted and positioned in place. Further, the protective wall 60 may also serve to guide the sap flow when the sap flows via the sensor unit 50 of the microneedle probe 1.

In addition, according to the exemplary embodiment of the present invention, cavities 20 may be installed in the substrate 10. The cavity 20 may be formed at the position where the sensor unit 50 of the substrate 10 is installed. A suspension 40 may be installed at an upper side of the cavity 20 in order to install the sensor unit 50 at the upper side of the cavity 20. The sensor unit 50 is installed on the suspension 40, and the suspension 40 is made of a material having low thermal conductivity, such that the suspension 40 may be configured to, together with the cavity 20, minimize heat transfer between the sensor unit 50 and the substrate 10.

In one exemplary embodiment, the suspension 40 may be formed as a thin film made of anodized aluminum oxide and silicon nitride (SiN), and the suspension 40 may be positioned at the upper side of the cavity 20.

The anodized aluminum oxide refers to an aluminum substrate having nano-size pores regularly arranged in an aluminum surface oxidized by anodizing aluminum, and the silicon nitride has high strength, a small coefficient of thermal expansion, and excellent heat-resistant and impact-resistant properties, and as a result, the thin film made of the anodized aluminum oxide and the silicon nitride may effectively prevent heat transfer between the sensor unit 50 and the substrate 10.

Contact pads 90 for wire bonding may be installed by installing BUS lines 70 and 80 for supplying a current to the sensor unit 50, connecting the BUS lines 70 and 80 to an external terminal, and packaging the BUS lines.

The BUS line 70 connected to the heater 53 of the sensor unit 50 and the BUS line 80 connected to the temperature measuring sensors 51 and 52 may be configured as low-resistance BUS lines.

A sap flow measuring device may be configured by using the microneedle probe 1 for measuring a sap flow in a plant.

The sap flow measuring device according to an exemplary embodiment of the present invention may include a current generating unit which generates a current; a power supply unit which supplies power required to operate the current generating unit; the microneedle probe 1 which receives the current from the current generating unit and constitutes a measurement circuit by being inserted into a plant and coming into contact with sap in a xylem; and a control unit which calculates sap flow density (sap flux density) based on a value measured by the microneedle probe 1. Here, the values measured by the microneedle probe 1 may be resistance values in the temperature measuring sensors 51 and 52 and the amount of change in resistance values.

In the sap flow measuring device of the present invention, the heater 53 of the sensor unit 50 installed on the microneedle probe 1 forms a heat field by being supplied with the current and continuously generating heat, and a temperature distribution in the temperature measuring sensors 51 and 52 of the sensor unit 50 installed on the microneedle probe 1 is changed by the sap flow, such that the sap flow density may be measured based on a ratio of the temperature, which is measured by the sensors 51 and 52, to the resistance.

There may be a configuration in which the multiple microneedle probes 1 are provided to calculate sap flows at several points in the plant. In this case, it is possible to improve reliability of the measured values.

FIGS. 3A to 3H are views illustrating cross sections in the width direction of the microneedle probe 1 for explaining a process of manufacturing the microneedle probe 1 according to the exemplary embodiment of the present invention. However, the protective walls 60 illustrated in FIGS. 3E to 3H are illustrated in a state of being rotated by 90 degrees in order to improve visibility because other constituent elements are hidden and invisible by the protective walls 60 if the protective walls 60 are illustrated in a cross sectional view in the width direction. Referring to FIGS. 3A to 3H, the microneedle probe 1 according to the exemplary embodiment of the present invention may be manufactured through the following MEMS process.

Figure 3A:
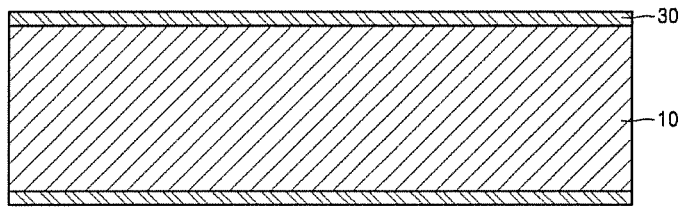
FIGS. 3A to 3H are views illustrating cross sections in a width direction of the microneedle probe for explaining a process of manufacturing the microneedle probe according to the exemplary embodiment of the present invention.
Figure 3B:
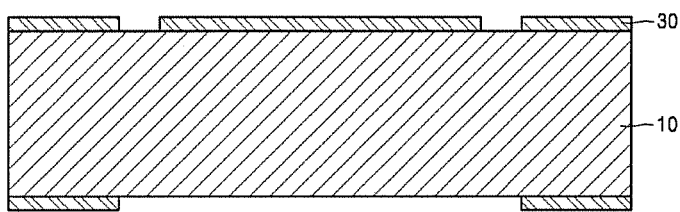
Figure 3C:
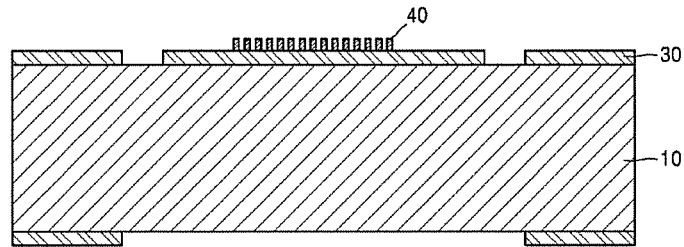
Figure 3D:
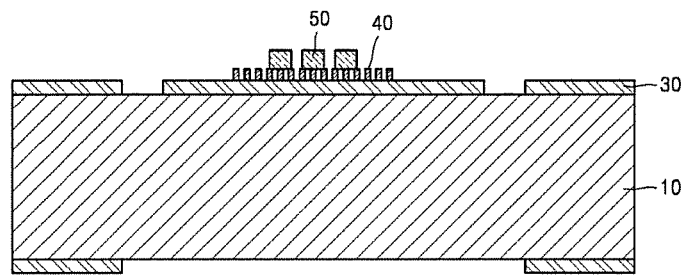

First, silicon oxidation layers 30 are formed on surfaces of the substrate 10 configured as a silicon wafer of 500 μm. Here, the silicon oxidation layer 30 may have a thickness of 0.5 μm (FIG. 3A). Next, in FIG. 3B, a needle shape may be made by performing upper patterning on the silicon oxidation layer 30 of the substrate 10, and a deep etching area may be formed by performing lower patterning. In FIG. 3C, a porous thin film, particularly, an anodized aluminum oxide (AAO) porous thin film may be formed. Here, the thin film may have a thickness of 200 nm, and the anodized aluminum oxide porous thin film is the suspension 40. Next, the sensor unit 50 having a thickness of 150 nm is patterned on the anodized aluminum oxide thin film (FIG. 3D). The sensor unit 50 may be made of gold.

Figure 3E:
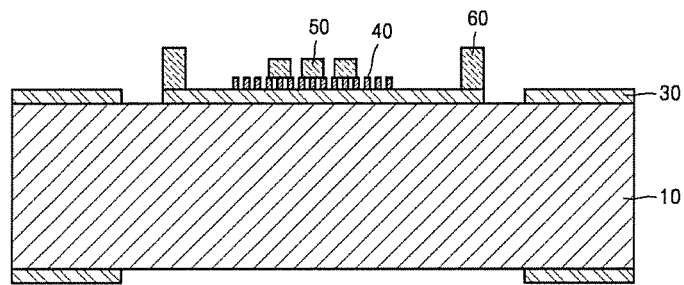
Figure 3F:
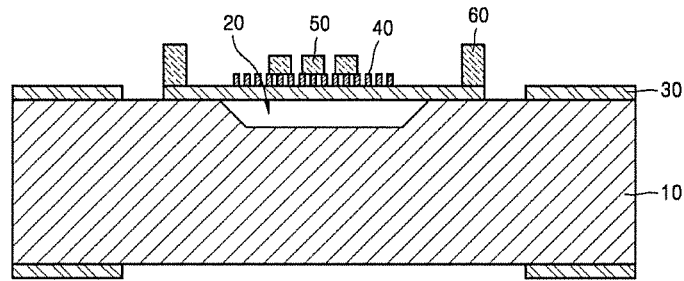
Figure 3G:
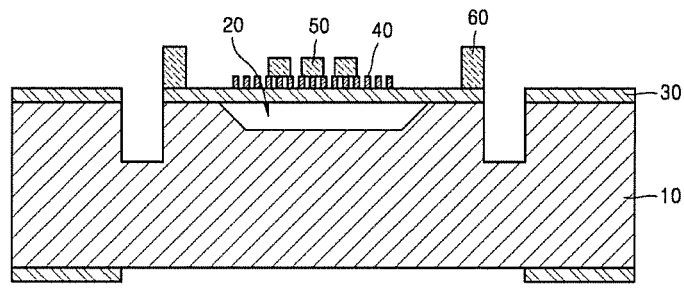
Figure 3H:
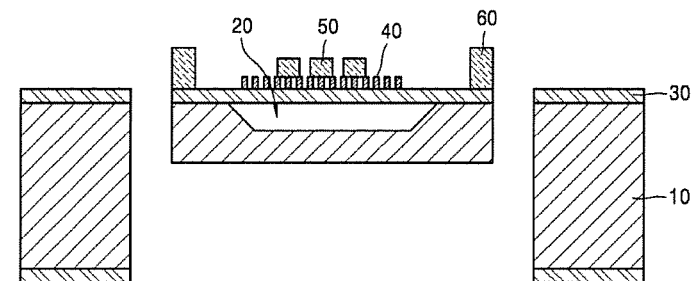

Next, the protective wall 60 may be thickly patterned with a polymer or nickel structure at the front side and/or the rear side of the sensor unit 50 in the longitudinal direction of the substrate 10. The protective wall 60 may be formed to have a thickness of 50 μm to protect the sensor unit 50, allow the microneedle probe 1 to be easily inserted into the plant body, and guide the sap flow (FIG. 3E). In FIG. 3F, the cavity 20 is formed by etching at a part of the substrate 10 which is positioned below the anodized aluminum oxide thin film, and a depth of the cavity 20 is 50 μm. Next, deep reactive ion etching may be performed with a thickness of 250 μm in order to implement an upper needle shape (FIG. 3G). In FIG. 3H, deep reactive ion etching may be performed with a thickness of 250 μm in order to implement a lower deep etching region.

In addition, to sharpen one end portion of the substrate 10, a sharpening process, which adjusts a degree, to which one end portion of the substrate 10 is sharp, may be performed by silicon impurity doping and selective etching.

While the present invention has been described with reference to the aforementioned exemplary embodiment, various modifications or alterations may be made without departing from the subject matter and the scope of the invention. Accordingly, the appended claims include the modifications or alterations as long as the modifications or alterations fall within the subject matter of the present invention.

What is claim is:

1. A microneedle probe configured to be inserted into a xylem of a plant to measure a flow of sap in the xylem, the microneedle probe comprising:

a substrate extending along a longitudinal axis between a first end and a second end, the substrate defining a single insertion portion that is configured to be inserted into the xylem of the plant when the microneedle probe is inserted into the xylem of the plant;
a sensor unit disposed on the single insertion portion of the substrate and configured to measure the flow of sap;
wherein the sensor unit includes two temperature measuring sensors which are separated from each other in a direction which is perpendicular to the longitudinal axis of the substrate, and a heater which is positioned between the two temperature measuring sensors; and
wherein a distance between the two temperature measuring sensors is less than 1 mm.

2. The microneedle probe of claim 1, wherein the single insertion portion of the substrate has a microscale in a thickness direction and a width direction.

3. The microneedle probe of claim 1, wherein a width of the single insertion portion is less than 1 mm and a thickness of the insertion portion is less than 1 mm.

4. The microneedle probe of claim 3, wherein the longitudinal axis of the substrate is perpendicular to a direction of the flow of sap in the xylem when the single insertion portion of the substrate is inserted into the xylem of the plant.

5. The microneedle probe of claim 4, wherein the sensor unit is fully inserted into the flow of sap in the xylem when the single insertion portion of the substrate is inserted into the xylem of the plant.

6. The microneedle probe of claim 5, wherein the temperature measuring sensor of the sensor unit uses a temperature coefficient of resistance of a metal pattern.

7. The microneedle probe of claim 1, wherein the first end of the substrate is sharpened.

8. The microneedle probe of claim 3, the substrate further comprising a thin portion position proximate to the first end of the substrate and a thick portion position between the thin portion and the second end of the substrate, a thickness of the thin portion being less than a thickness of the thick portion.

9. The microneedle probe of claim 3, the substrate further comprising a base proximate to the second end, the base defining a tapered edge such that a width of the substrate at the base gradually increases along the longitudinal axis of the substrate.

10. The microneedle probe of claim 3, further comprising a second sensor unit disposed on the single insertion portion of the substrate and configured to measure the flow of sap;
wherein the second sensor unit includes two temperature measuring sensors which are separated from each other in a direction which is perpendicular to the longitudinal axis of the substrate, and a heater which is positioned between the two temperature measuring sensors.

11. The microneedle probe of claim 3, further comprising:
a cavity which is formed in the single insertion portion of the substrate; and
a suspension which is disposed on the cavity,
wherein the sensor unit is disposed on the suspension such that a heat transfer between the sensor unit and the substrate is inhibited.

12. The microneedle probe of claim 11, wherein the suspension comprises a thin film of anodized aluminum oxide and silicon nitride.

13. The microneedle probe of claim 3, further comprising:
a contact pad which connects a BUS line, which is connected to the sensor unit, to an external terminal and packages the BUS line.

14. The microneedle probe according to claim 3, further comprising:
a current generating unit which generates a current;
a power supply unit which supplies power required to operate the current generating unit;
wherein the microneedle probe receives the current from the current generating unit and constitutes a measurement circuit by being inserted into a plant and coming into contact with sap in a xylem; and
a control unit which calculates sap flow density based on a value measured by the sensor unit of the microneedle probe.

15. A microneedle probe for measuring a sap flow in a plant, the microneedle probe comprising:
a substrate which is inserted into the plant and has a microscale in a thickness direction and a width direction; and
a sensor unit which is installed on a single insertion portion of the substrate inserted into the plant for measuring a sap flow;
wherein the sensor unit includes two temperature measuring sensors which are separated from each other in a direction which is perpendicular to a longitudinal direction of the substrate, and a heater which is positioned between the two temperature measuring sensors; and
wherein a distance between the two temperature measuring sensors is less than 1 mm.

16. The microneedle probe of claim 15, wherein at the point of installation of the sensor unit, a width of the substrate is less than 1 mm and a thickness of the single insertion portion is less than 1 mm.

17. The microneedle probe of claim 16 wherein the longitudinal axis of the substrate is perpendicular to a direction of the flow of sap when the sensor unit it inserted into the plant.

* * * * *